US00PP08217P

United States Patent [19]

Christensen

[11] Patent Number: Plant 8,217

[45] Date of Patent: May 4, 1993

[54] ROSE PLANT JACMIST

[75] Inventor: Jack E. Christensen, Ontario, Calif.

[73] Assignee: Bear Creek Gardens, Inc., Medford, Oreg.

[21] Appl. No.: 774,267

[22] Filed: Oct. 10, 1991

[51] Int. Cl.[5] ..... A01H 5/00

[52] U.S. Cl. ..... Plt./11

[58] Field of Search ..... Plt. 11, 12, 13, 22

*Primary Examiner*—James R. Feyrer

*Assistant Examiner*—E. F. McElwain

*Attorney, Agent, or Firm*—Klarquist, Sparkman, Campbell, Leigh & Whinston

[57] ABSTRACT

A hybrid tea rose created by crossing the variety KORwillig with an unnamed seedling is characterized by its profuse, unique red and white flower color that is most evident on the reverse of the petals, its upright vigorous growth, its susceptibility to mildew but resistance to rust and its dark green, glossy foliage.

1 Drawing Sheet

The present invention relates to a new and distinct variety of rose plant of the hybrid tea class which was originated by me by crossing the variety KORwillig, with an unnamed seedling.

The primary objective of this breeding was to produce a new rose variety having the vigor and dark green leathery foliage of KORwillig combined with the profuse flowering of the unnamed seedling. The objective was substantially achieved along with other desirable improvements as evidenced by the following unique combination of characteristics which are outstanding in the new variety and which distinguish it from its parents, as well as from all other varieties of which I am aware:

1. Unique red and white flower color that is most evident on the reverse of the petals;
2. Upright, vigorous growth;
3. Susceptibility to mildew but resistance to rust; and
4. Dark green, glossy foliage.

Asexual reproduction of this new variety by budding, as performed at Wasco and Somis, Calif., shows that the foregoing characteristics and distinctions come true to form and are established and transmitted through succeeding propagation.

The accompanying color photograph shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—KORwillig.

*Pollen parent.*—Unnamed seedling.

Classification:

*Botanical.*—*Rosa Hybrida.*

*Commercial.*—Hybrid Tea.

FLOWER

Observations made from specimens grown Somis, Calif. in April-June 1991.

Blooming habit: Recurrent.

Bud:

*Size.*—1½ inches when the petals start to unfurl.

*Form.*—Long, pointed ovoid.

*Color.*—When sepals first divide, bud color is Red Group 46B that blends into white Group 155D. When half blown, the upper sides of the petals are Red Group 45B; and the lower sides of the petals are Red Group 45B on the petal edges with white group 155D on the rest of the petal.

*Sepals.*—Color: Green Group 139C with a reddish cast. Surface texture: Covered in fine hairs. There are three heavily appendaged sepals. There are two unappendaged sepals with hairy edges.

*Receptacle.*—Color: Green Group 143B with reddish cast. Shape: Funnel. Size: Small, ⅜ inch by ⅜ inch. Surface: Smooth.

*Peduncle.*—Length: Short, 2½ inches. Surface: Prickly. Color: Medium green and bronzy. Strength: Stiff, erect.

Bloom:

*Size.*—Medium. Average open size is 3½ to 4 inches.

*Borne.*—Singly.

*Stems.*—Medium, 12 inches to 14 inches.

*Form.*—When first open: High centered. Permanence: Flattens, outer petals curl back.

*Petalage.*—Number of petals under normal conditions: 30.

*Color.*—The upper side of the petals is red Group 45B. The reverse side of the petals is Red Group 45B on the petal edges with White Group 155D elsewhere. The base of petals has a small, white, half moon, ⅜ inches by ⅜ inches. The major color on the upper side is Red Group 45B.

*Variegations.*—None.

*Discoloration.*—No change in the general tonality at the end of the first day through the end of the third day. By the fifth and sixth days, the petals begin to dry and stay on the plant.

*Fragrance.*—Slight.

Petals:

*Texture.*—Thick, leathery.

*Shape.*—Round.

*Form.*—Tips slightly recurved.

*Arrangement.*—Imbricated, with a few petaloids in the center.

*Persistence.*—Hang on and dry.

*Lastingness.*—On the plant: Long, 5 to 6 days. As a cut flower: Long, 6 to 8 days.

Reproductive parts:

*Anthers.*—Size: Medium. Quantity: Many. Color: Yellow. Arrangement: Regular around the styles.

*Filaments.*—Color: Yellow.

*Pollen.*—Color: Lemon-yellow.

*Styles.*—Color: Red.

*Stigmas.*—Color: Greenish-white.

Form: Bush.

Growth: Vigorous, upright branching.

Foliage:

*Number of leaflets on normal mid-stem leaves.*—5.

*Size.*—Large, 6 inches by 5 inches

*Quantity.*—Normal.

*Color.*—New foliage: Reddish. Old foliage: Dark, glossy, green.

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Rough, with prickles.

*Stipules.*—Medium (¾ inch), bearded.

*Disease resistance.*—Susceptible to mildew but resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its unusual red and white flower color that is most evident on the reverse of the petal, its resistance to rust and susceptibility to powdery mildew, its vigorous upright growth habit and its dark green glossy foliage.

* * * * *

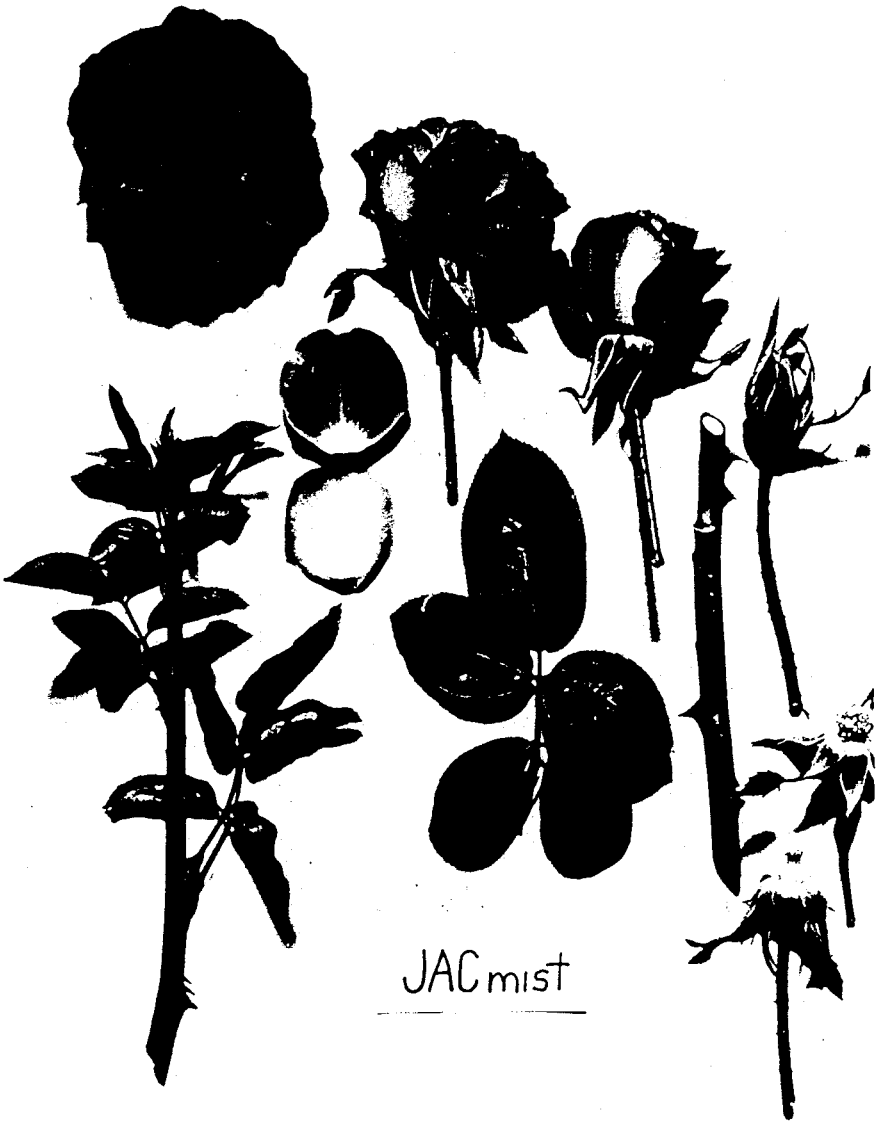
JAC mist